(12) United States Patent
Schultz et al.

(10) Patent No.: US 11,033,714 B2
(45) Date of Patent: Jun. 15, 2021

(54) CATHETER WITH BIASED AND DISCRETE DEFLECTION CHARACTERISTICS AND RELATED METHODS

(71) Applicant: BIOSENSE WEBSTER (ISRAEL) LTD., Yokneam (IL)

(72) Inventors: Jeffrey William Schultz, Chino, CA (US); Mark T. Stanley, Seal Beach, CA (US); Daniele Ghidoli, Laguna Hills, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 386 days.

(21) Appl. No.: 15/844,301

(22) Filed: Dec. 15, 2017

(65) Prior Publication Data

US 2019/0184138 A1 Jun. 20, 2019

(51) Int. Cl.
| | |
|---|---|
| *A61M 25/01* | (2006.01) |
| *A61B 5/042* | (2006.01) |
| *A61B 18/14* | (2006.01) |
| *A61M 25/00* | (2006.01) |
| *A61B 18/00* | (2006.01) |

(52) U.S. Cl.
CPC ....... *A61M 25/0144* (2013.01); *A61B 5/0422* (2013.01); *A61B 18/1492* (2013.01); *A61M 25/0009* (2013.01); *A61M 25/0136* (2013.01); *A61M 25/0147* (2013.01); *A61B 2018/00577* (2013.01); *A61B 2018/00839* (2013.01)

(58) Field of Classification Search
CPC .......... A61M 25/0147; A61M 25/0138; A61M 2025/0161; A61M 25/0054; A61M 25/0105; A61M 2025/0063; A61M 25/0102; A61M 25/0144; A61M 25/0152; A61M 1/0055; A61M 1/0056
See application file for complete search history.

(56) References Cited

U.S. PATENT DOCUMENTS

| | | | |
|---|---|---|---|
| 6,475,184 B1 | 11/2002 | Wang et al. | |
| 6,749,560 B1 * | 6/2004 | Konstorum | A61B 1/00071 600/139 |
| 6,890,329 B2 | 5/2005 | Carroll et al. | |
| 7,708,704 B2 | 5/2010 | Mitelberg et al. | |
| 7,972,323 B1 | 7/2011 | Bencini et al. | |
| 8,357,152 B2 | 1/2013 | Govari et al. | |
| 8,376,991 B2 | 2/2013 | Kauphusman et al. | |
| 8,708,953 B2 | 4/2014 | Salahieh et al. | |
| 8,728,075 B2 | 5/2014 | Wu et al. | |

(Continued)

OTHER PUBLICATIONS

International Preliminary Report on Patentability dated Jun. 16, 2020 issued in corresponding International Application No. PCT/US2018/065234, 7 pages.

*Primary Examiner* — Emily L Schmidt
(74) *Attorney, Agent, or Firm* — Lewis Roca Rothgerber Christie LLP

(57) ABSTRACT

A deflectable catheter with biased deflection characteristics has an elongated catheter body having a micro-injection molded spine that is configured with a center core, outwardly extending opposing struts, and one or more sets of longitudinally-aligned and discrete fins, wherein the struts resist deflection of the spine in a first plane and bias deflection of the spine in a second plane, wherein parameters of the discrete fins define deflection characteristics of the spine in the second plane.

15 Claims, 7 Drawing Sheets

(56) References Cited

U.S. PATENT DOCUMENTS

| | | |
|---|---|---|
| 9,162,046 B2 | 10/2015 | Hill et al. |
| 2002/0068868 A1 | 6/2002 | Thompson et al. |
| 2002/0082585 A1 | 6/2002 | Carroll et al. |
| 2010/0069882 A1 | 3/2010 | Jennings et al. |
| 2010/0082000 A1 | 4/2010 | Honeck et al. |
| 2011/0130648 A1 | 6/2011 | Beeckler et al. |
| 2015/0297863 A1 | 10/2015 | Hannon et al. |
| 2018/0001058 A1* | 1/2018 | Schlesinger ...... A61M 25/0147 |

* cited by examiner

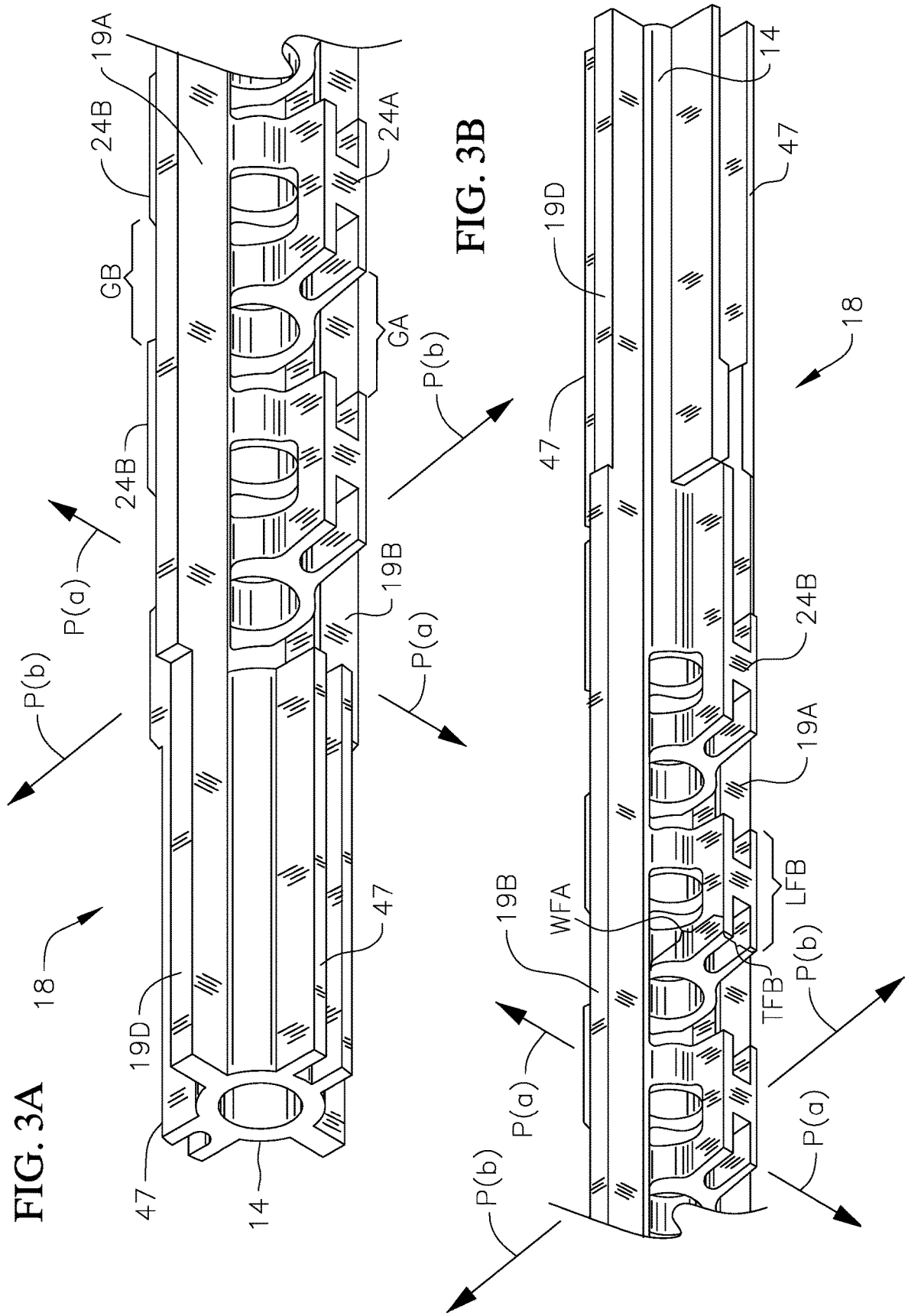

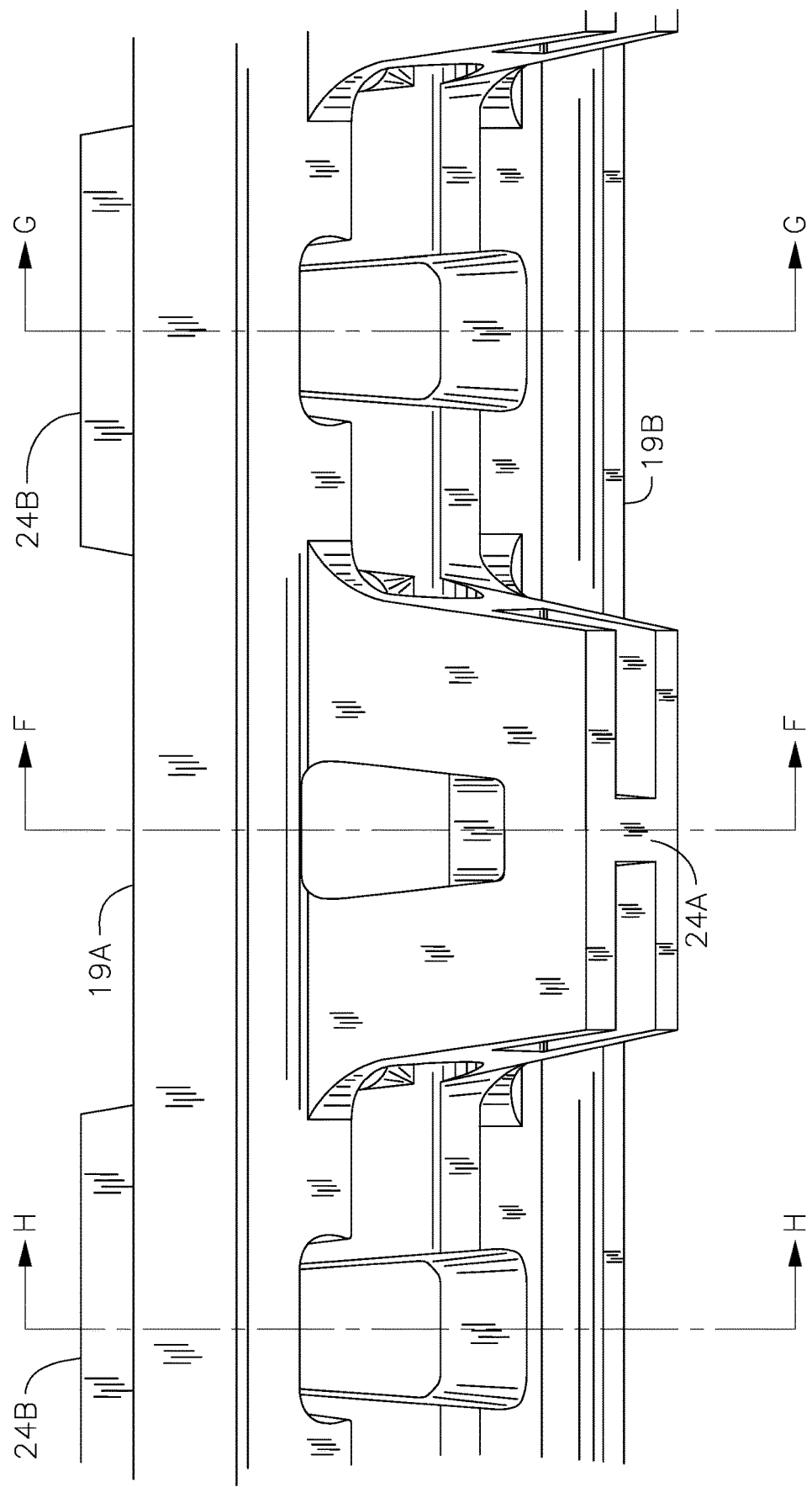

CATHETER WITH BIASED AND DISCRETE DEFLECTION CHARACTERISTICS AND RELATED METHODS

FIELD OF INVENTION

The present invention relates to electrophysiologic (EP) catheters, in particular, EP catheters for mapping and/or ablating tissue.

BACKGROUND

Electrode catheters have been in common use in medical practice for many years. Diagnosis and treatment of cardiac arrythmias by means of electrode catheters include mapping the electrical properties of heart tissue and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall.

In a two-step procedure-mapping followed by ablation-electrical activity at locations within the heart is typically sensed and measured by advancing a catheter containing one or more electrical sensors (or electrodes) into the heart, and acquiring data at a multiplicity of locations. These data are then utilized to select the tissue target areas at which ablation is to be performed.

In use, the electrode catheter is inserted into a major vein or artery, e.g., the femoral artery, and then guided into the chamber of the heart which is of concern. A reference electrode is provided, generally taped to the patient's skin or provided on the ablation catheter or another catheter. Radio frequency (RF) current is applied to the ablation electrode of the catheter, and flows through the surrounding media, i.e., blood and tissue, toward the reference electrode. The distribution of current depends on the amount of electrode surface in contact with the tissue, as compared to blood which has a higher conductivity than the tissue.

Success of the mapping and ablation procedures depends in a large part on the proper placement of the catheter electrode(s) which are often carried on the distal tip. Different degrees and configurations of deflection and the improved control of the deflection of the catheter are therefore desirable in a deflectable catheter.

Moreover, construction of conventional catheters may be described as assembly from the "outside in," where the catheter tubing is one of the first components to be handled, followed by wires and cables that are fed through the one or more lumens of the tubing, typically blindly by the assembly technician without visibility into the lumens which can result in damage to the wires and cables. Such manual assembly is labor intensive and thus costly. With the advent of micro-injection-molding enabling very small components and configurations to be injected molded with high accuracy, parts and portions of electrophysiology catheters may be manufactured cost-effectively for high-volume production, and also simplify catheter assembly to further reduce labor and cost.

Accordingly, there is a desire to provide a catheter with improved deflection characteristics and customization, and a method of assembly that includes micro-injection molding to advance construction more toward an "inside out" manner which can reduce the cost of assembly and also risk of damage to parts and components during assembly.

SUMMARY OF THE INVENTION

In some embodiments of the present invention, a deflectable electrophysiology catheter built and assembled in an "inside out" manner has an elongated catheter body with a spine that is micro-injection molded from a flexible material and assembled with puller wires, tubings, lead wires and/or cables to form a spine assembly before the spine assembly is inserted into or otherwise covered by a tubing structure to form the catheter body. The spine is micro-injection molded with a center core, two opposing struts, and a first set of longitudinally-aligned fins along at least a first section of the spine. The opposing struts extend outwardly from the core in defining a plane P(a) generally bisecting the spine along the longitudinal direction into a portion N(a) and a portion N(b). The struts are configured to resist deflection of the spine within the plane P(a) and bias deflection within a plane P(b) generally perpendicular to the plane P(a). The first set of fins extend outwardly from the core in the portion N(a) of the spine and are coextensive with the plane P(b). Each of the fins of the first set has a first predetermined length in the longitudinal direction and is separated from an adjacent fin of the first set by a first predetermined gap space to provide the spine with a first predetermined deflection curvature within the plane P(b) in the direction of the first set of fins in the first section of the spine. The catheter includes a control handle configured to deflect the catheter body.

In some embodiments, the deflectable catheter includes a second set of longitudinally-aligned fins along the first section of the spine in the portion N(b), the second set of fins generally opposite of the first set of fins in the portion N(a) of the spine and coextensive with the plane P(b).

In some embodiments, each of the fins of the second set has a second predetermined length in the longitudinal direction and is separated from an adjacent fin of the second set by a second predetermined gap space to provide the spine with a second predetermined deflection curvature within the plane P(b) in the direction of the second set of fins in the first section of the spine, wherein the second predetermined length is generally equal to the first predetermined length.

In some embodiments, each of the fins of the second set has a second predetermined length in the longitudinal direction and is separated from an adjacent fin of the second set by a second predetermined gap space to provide the spine with a second predetermined deflection curvature within the plane P(b) in the direction of the second set of fins in the first section of the spine, wherein the second predetermined gap space is generally equal to the first predetermined gap space.

In some embodiments, the spine is provided with a second predetermined deflection curvature within the plane P(b) in the direction of the second set of fins, wherein the second predetermined deflection curvature is generally equal to the first predetermined deflection curvature within the plane P(b) in the direction of the first set of fins.

In some embodiments, each of the fins of the second set has a second predetermined length in the longitudinal direction, wherein the second predetermined length is different from the first predetermined length of the first set of fins.

In some embodiments, each of the fins of the second set is separated from an adjacent fin of the second set by a second predetermined gap space, wherein the second predetermined gap space is different from the first predetermined gap space of the first set of fins.

In some embodiments, the spine is provided with a second predetermined deflection curvature within the plane P(b) in the direction of the second set of fins, wherein the second predetermined deflection curvature is different from the first predetermined deflection curvature within the plane P(b) in the direction of the first set of fins.

In some embodiments, one of the struts and one set of longitudinally-aligned fins define a quadrant space therebetween that is covered by a portion of the outer covering.

In some embodiments, the deflectable catheter includes a tensile member passing through the quadrant space.

In some embodiments, the deflectable catheter includes a tubing passing through the quadrant space.

In some embodiments, the deflectable catheter includes an insert that spans across at least one gap space between at least two fins of the first set.

In some embodiments, the insert is received in a notch formed in each of the fins.

In some embodiments, the core of the spine has a through-hole in the longitudinal direction.

In some embodiments, the spine has another set of fins extending outwardly from the core in another (second) section of the spine and coextensive with the plane P(b), and each of the fins of the another set has another predetermined length in the longitudinal direction different from the first predetermined length of the fins of the first set.

In some embodiments, the spine has another set of fins extending outwardly from the core in another (second) section of the spine and coextensive with the plane P(b), and each of the fins of the another set is separated from an adjacent fin of the another set by another predetermined gap space that is different from the first predetermined gap space of the fins of the first set.

In some embodiments of the present invention, a method of manufacturing a deflectable catheter body, comprises forming the spine with micro-injection molding, assembling a spine assembly by placing a first puller wire to extend along the catheter body in a first quadrant space of the spine defined between one of the struts and the first set of fins, and circumferentially surrounding the spine assembly with a cover along the length of the catheter body.

In some embodiments, forming a spine further comprises forming a second set of longitudinally-aligned fins along the first section S(a) of the spine in the portion N(b), the second set of fins generally opposite of the first set of fins in the portion N(a) of the spine and generally co-extensive with the second plane P(b).

In some embodiments, assembling the spine assembly further comprises placing a second puller wire to extend along the catheter body in a second quadrant defined between the other of the struts and the second set of fins.

In some embodiments, assembling the spine assembly includes placing an insert to connect at least two fins of the first set.

In some embodiments, assembling the spine assembly includes placing a first insert to connect at least two fins of the first set and placing a second insert to connect at least two fins of the second set.

In some embodiments, forming a spine includes forming a through-hole in the core of the spine.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 3A is a perspective top view of a spine including its distal end, according to one embodiment.

FIG. 3B is a perspective bottom view of the spine of FIG. 3A.

FIG. 4 is a detailed perspective view of a spine, according to one embodiment.

DETAILED DESCRIPTION OF THE INVENTION

Figure 1:
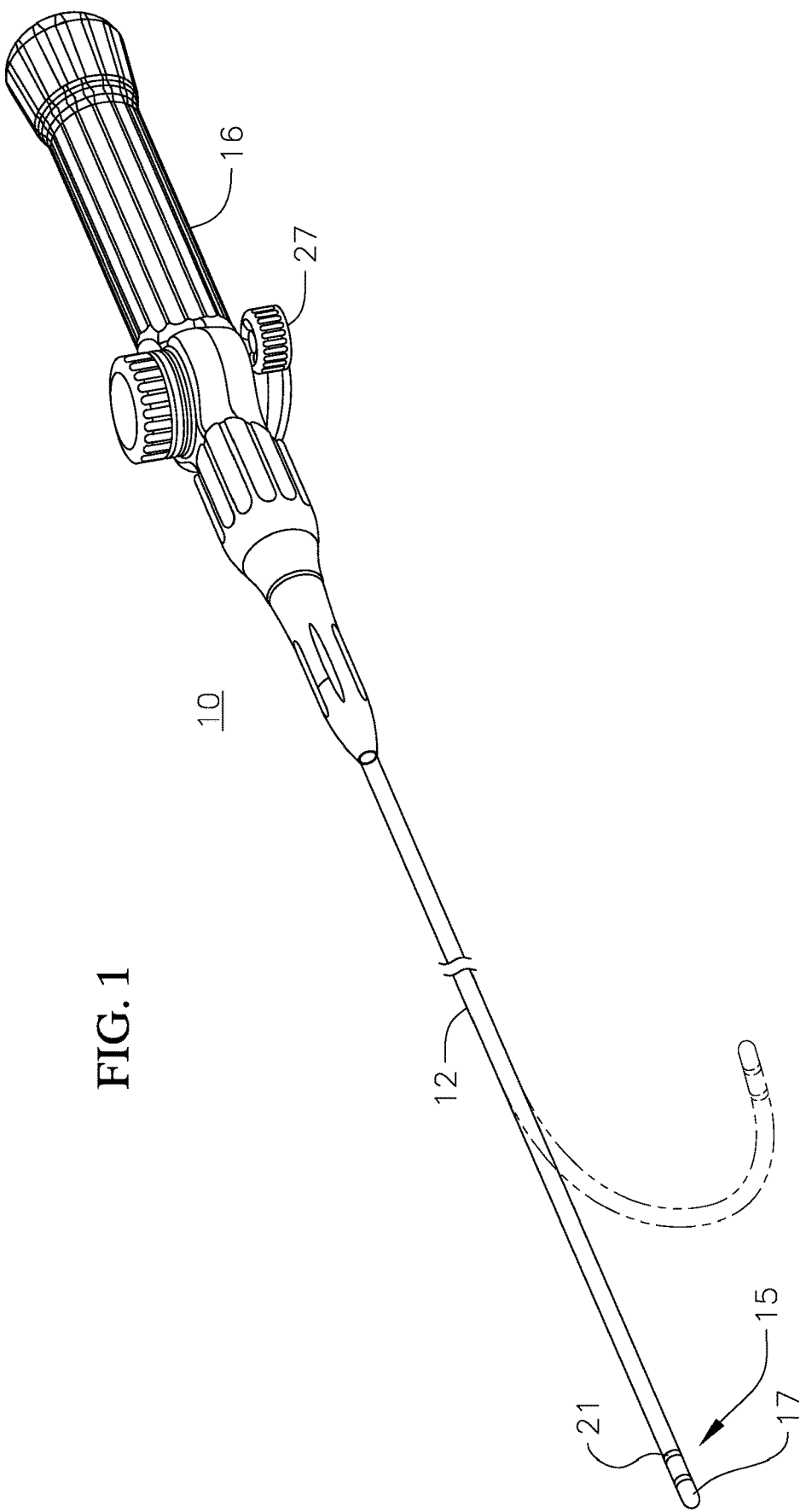
FIG. 1 is a perspective view of a catheter of the present invention, according to one embodiment.

FIG. 1 illustrates an embodiment of a catheter 10 with improved deflection characteristics, including biased deflection in one or more sections of the catheter. The catheter advantageously includes an elongated, injection-molded support structure or "spine" to provide symmetrical bi-directional deflection within a plane and/or asymmetrical deflection in such one or more sections of its elongated deflectable body 12, and a control handle 16 proximal of the deflectable body 12 for actuating and controlling deflection of the one or more sections of the deflectable body 12. In some embodiments, the catheter also includes a distal section 15 with one or more electrodes, for example, a tip electrode 17 and a ring electrode 21.

Figure 2:
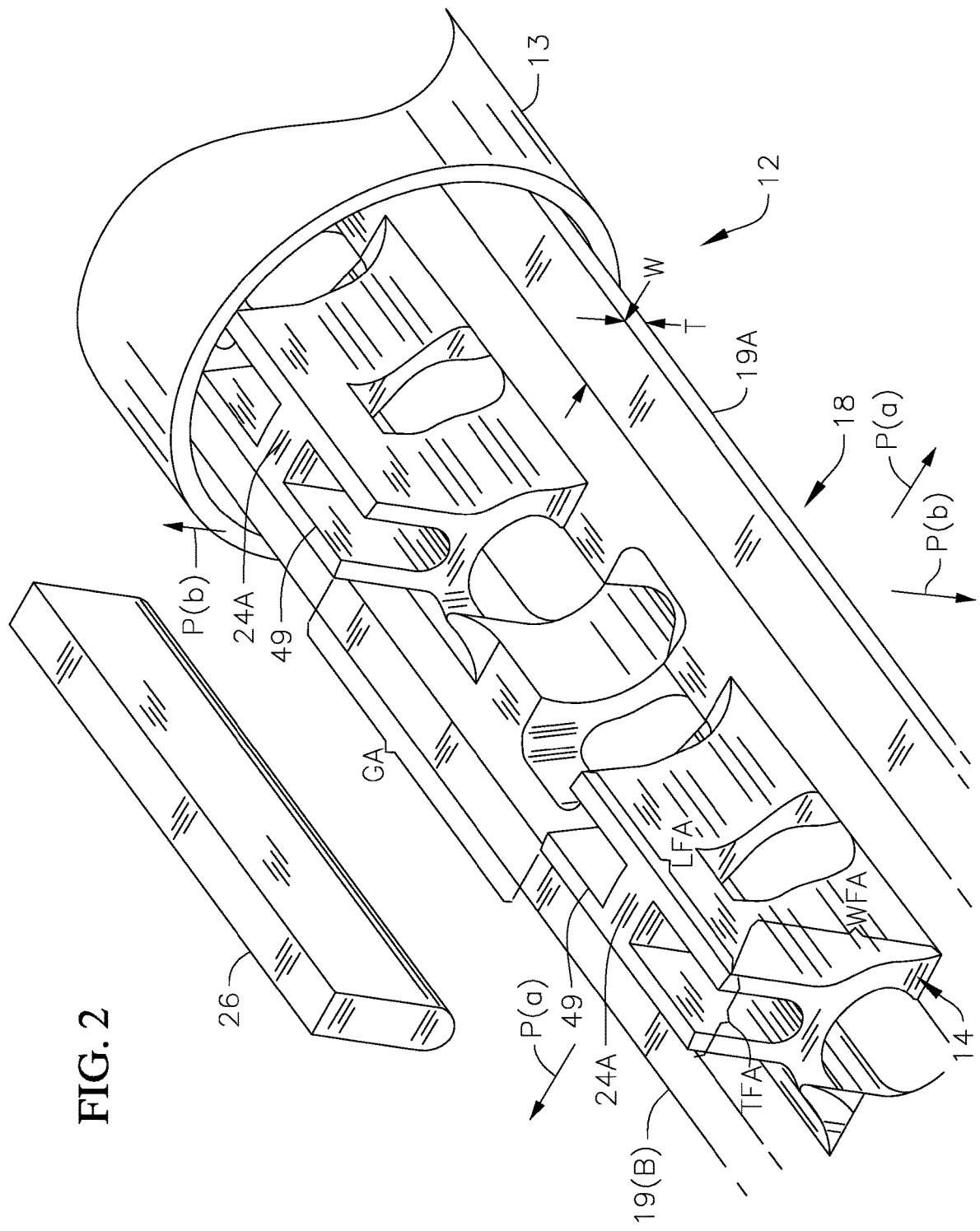
FIG. 2 is a perspective view of a catheter body with a spine, according to one embodiment, with part(s) broken away.

With reference to FIG. 2, the deflectable body 12 comprises an elongated flexible outer cover or tubing 13 of a nonconductive, biocompatible material, e.g., braided polyurethane, that circumferentially and longitudinally covers a support structure or spine 18 that spans a predetermined length of the deflectable body 12, for example, the entirety of the length or a portion of the length, as needed or appropriate. In the latter instance, the spine 18 may extend longitudinally through any section of the deflectable body 12 at any location, as needed or appropriate. In some embodiments, the deflectable body 12 may include multiple spine sections connected or situated longitudinally, with different spine sections having different deflection characteristics, as needed or appropriate.

Figure 5A:
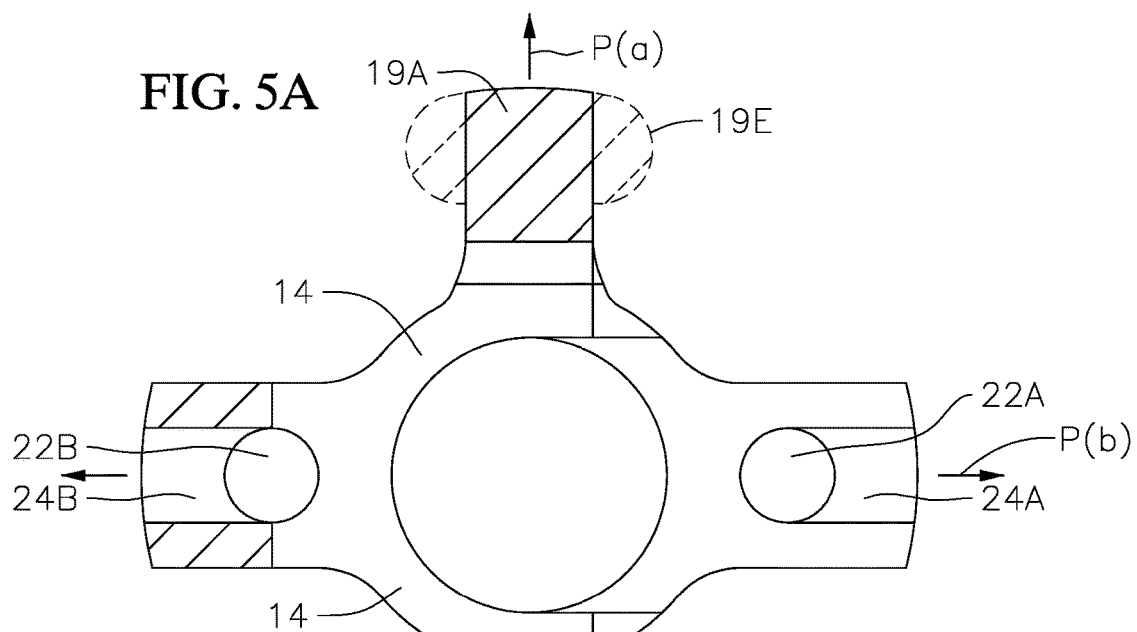
FIG. 5A is an end cross-sectional view of the spine of FIG. 4, taken along line G-G.
Figure 5B:
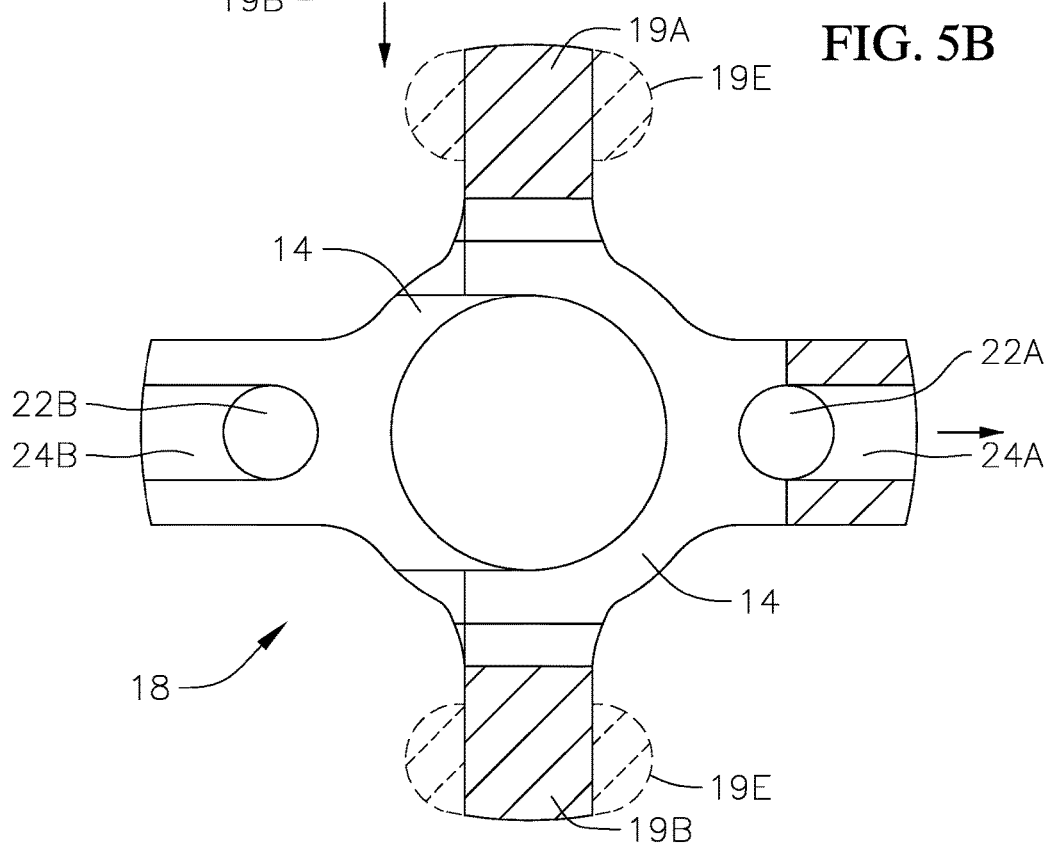
FIG. 5B is an end cross-sectional view of the spine of FIG. 4, taken along line F-F.
Figure 5C:
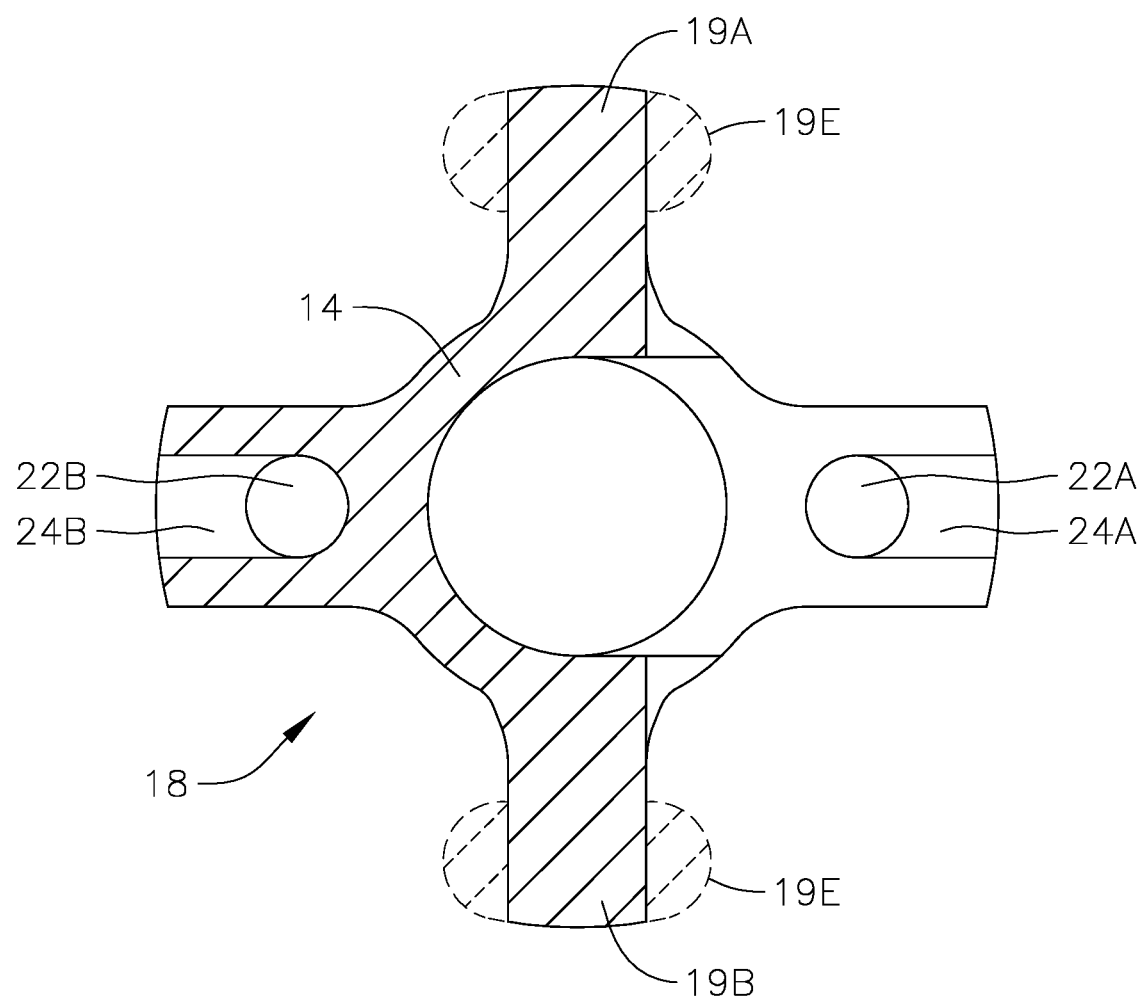
FIG. 5C is an end cross-sectional view of the spine of FIG. 4, taken along line H-H.
Figure 6:
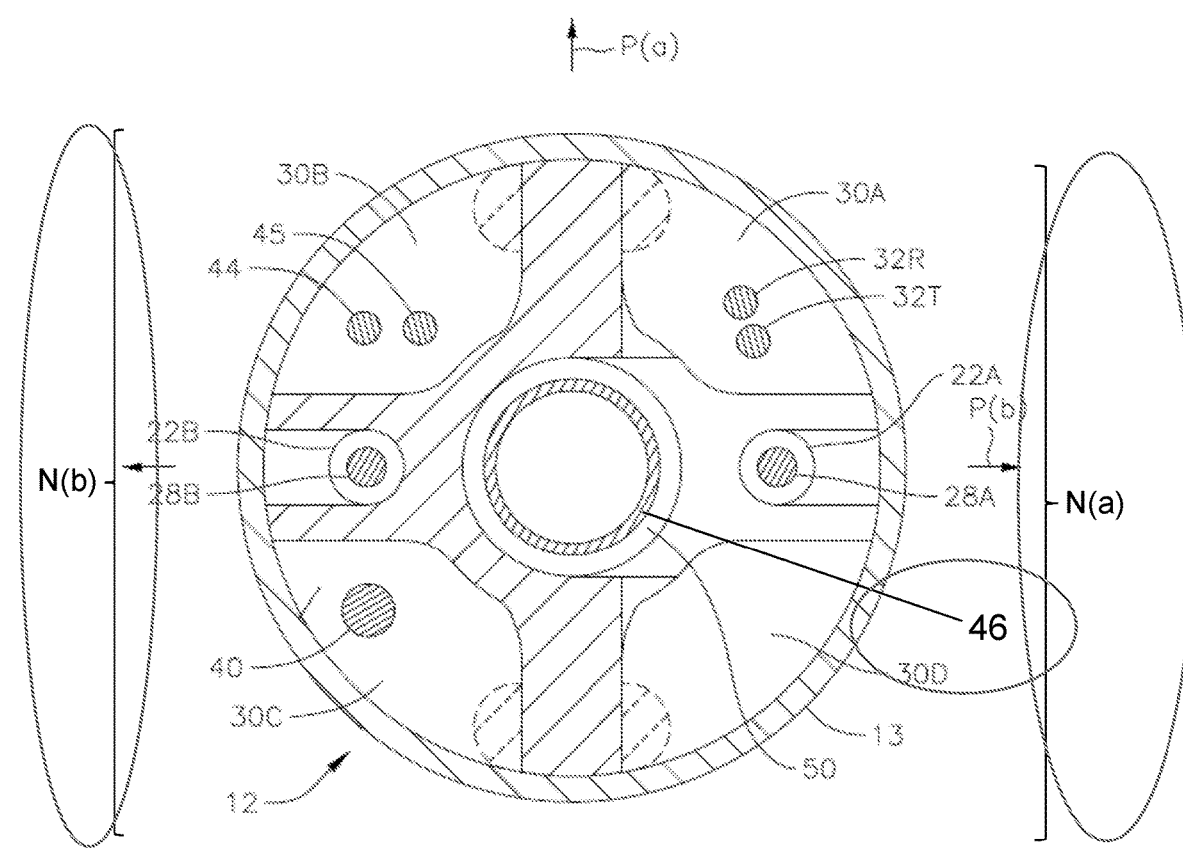
FIG. 6 is an end cross-sectional view of a catheter body with a spine and an outer cover, according to one embodiment.

With reference to FIG. 2, FIG. 3A and FIG. 3B, a spine 18 includes a core 14 and a first elongated ridge formation or "strut" 19A spanning longitudinally along the core 14 and extending outwardly from the core 14. In the illustrated embodiment, the spine 18 includes a second elongated ridge formation or "strut" 19B spanning longitudinally along the core 14 and extending outwardly but generally diametrically opposed to the first strut 19A, such that the struts 19A and 19B generally define a plane P(A) bisecting the deflectable body 12 along its length. Each strut may be defined by parameters, including, for example, a thickness T and a width W. As illustrated the struts have a generally rectangular cross-section. However, it is understood that the struts may have a variety of cross-sections, including a thicker end portion 19E, as shown in FIG. 5A and FIG. 5B, for increased rigidity to increase resistance to deflection in one direction or plane, and/or increase bias for deflection in another direction or plane. Each of the struts 19A and 19B resists compression and tension forces and thus resists deflection of the spine in the bisecting plane P(A) in advantageously biasing the spine 18 for deflection in a deflection plane P(B) that is generally perpendicular to the bisecting plane P(A). In the illustrated embodiment, the struts 19A and 19B have similar parameters for symmetrical deflection in the plane P(B), although it is understood by one of ordinary skill in the art that these struts may have different parameters between them, as needed or appropriate, e.g., for asymmetrical deflection in the plane P(B).

Approximately 90 degrees radially about the longitudinal axis of the spine 18 from the first struts 19A are a plurality or set of first discrete fins 24A that span longitudinally and extend outwardly from the core 14 and are separated by first devoid gaps GA between adjacent pairs. The fins and the core have a zig-zag pattern when the spine is viewed from the side. About 90 degrees radially about the longitudinal axis of the spine 18 from the second struts 19B (and diametrically opposing the first fins 24A) are the same plurality or set of second discrete fins 24B that span longitudinally and extend outwardly from the core 14 and are separated by second devoid gaps GB between adjacent pairs. As such, the first and second plurality of fins 24A and 24B generally lie in the deflection plane P(B), where the first gaps GA between first fins 24A decrease and second gaps 20B between second fins GB increase when the spine 18 deflects in a direction toward the fins 24A, and first gaps GA between the first fins 24A increase and second gaps GB between the second fins 24B decrease when the spine 18 deflects in a direction toward the second fins 24B.

In some embodiments, each first fin 24A has a counterpart second fin 24B at generally the same longitudinal location along the length of the spine 18. In some embodiments, the first fins 24A and the second fins 24B may be at different or nonmatching locations along the length of the spine 18, where, for example, in alternating locations along the length, as understood by one of ordinary skill in the art.

In the illustrated embodiments, each longitudinal set of first and second fins 24A and 24B, being discrete and separate, is uniformly defined by a set of parameters, including a thickness TF, a width WF, a length LF, and/or a longitudinal separation gap G from adjacent fins with a longitudinal set. In other embodiments, the first longitudinal set of fins 24A may be defined by a first set of parameters (e.g., TFA, WFA, LFA, and/or GA) that is different from a second set of parameters (e.g., TFB, WFB, LFB and/or GB) defining the second longitudinal set of fins 24B. In other embodiments, each or selected individuals of the first set and/or the second set of fins 24A, 24B may be defined by unique sets of parameters for different or customized deflection characteristics of the spine 18 (e.g., TFA≠TFB, WFA≠WFB, LFA≠LFB, and/or GA≠GB). For example, increasing the length LFA of one or more of the first fins 24A (or decreasing the separation gaps between adjacent fins) increases the stiffness in those sections of spine, thus affecting or increasing the curvature radius of deflection of the spine 18 in those sections in the direction of first fins 24A). Conversely, decreasing the length LFA of one or more first fins 24A (or increasing the separation gaps) increases flexibility in those sections of the spine and thus decreases the curvature radius of deflection of the spine 18 in those sections in the direction of the first fins 24A). As such, it is understood by one of ordinary skill in the art that different deflection characteristics along the length of the catheter, or for one or more sections thereof, can be achieved by adjusting selected parameters or combinations of selected parameters.

In some embodiments, deflection characteristics of the spine are also adjusted by one or more stiffening inserts 26 that effectively connect one or more pairs of longitudinally-adjacent fins 24A and 24B. Each insert 26 increases stiffness of the spine between the one or more connected pairs of fins by filling in and eliminating the devoid gap GA or GB which would have otherwise allowed the spine 18 to bend and deflect in that direction. In this regard, interfacing notches 49 are formed in adjacent fins to receive the inserts 26 which may be placed at one or more segments along the length of the spine 18 to increase the stiffness discretely in those one or more segments. In some embodiments, deflection characteristics are adjusted by one or more "single-gap" inserts, each having a length sufficient to span across and fill in a single gap between a pair of adjacent fins, where each fin has a notch 49 that faces a notch 49 of an adjacent fin. The insert 26 is constructed of a material that provides sufficient rigidity to resist deflection of the spine where the fins have received an insert. In other embodiments, deflection characteristics are adjusted by one or more "multi-gap" inserts, each having a suitable length and profile or configuration adapted to fill in two or more gaps between multiple pairs of adjacent fins.

The inserts 26 may be used in both sets of fins 24A and 24B, or they may be used in one set of fins 24A without the other set of fins 24B, as needed or desired, for different deflection characteristics. Different curvatures and deflection characteristics can be achieved with selective use and placement of one or more inserts along the length of the spine. For example, selective use and placement of one or more inserts can allow the catheter body to provide the most open curve profile in an offering of curves (e.g., where the spine allows for F curve in a product offering of B, D and F curves). Moreover, to adjust the deflection profile or characteristics of the spine, selective use and placement of one or more inserts can change the effective length of regional properties of the spine. By decreasing the effective length of the spine, a tighter deflection curve, for example, can be achieved.

It is understood that the one or more struts bias the spine to bend in a predefined direction. This direction may be on a pre-defined plane or be such that the curvature/deflection of the spine takes a three-dimensional curve profile.

With reference to FIG. 5A, FIG. 5B, FIG. 5C and FIG. 6, to effectuate deflection in the deflection plane P(B) in the direction of the first fins 24A, a longitudinally-aligned through-hole 22A is provided in each first fin which together define or trace a first longitudinal "lumen-like" path along which a first puller wire 28A passes. For bi-directional deflection, a longitudinally-aligned through-hole 22B is provided in each second fin 24B which together define or trace a second longitudinal "lumen-like" path along which a second puller wire 28B passes.

Proximal ends of the first and second puller wires are anchored in the control handle 16 as known in the art, where the puller wires are actuated by a deflection control 27 configured for manipulation by an operator, as understood by one of ordinary skill in the art, to deflect the deflectable body 12 within the deflection plane P(B) toward either the side of the first fins 24A by drawing the first puller wire 28A proximally or the side of the second fins 24B by drawing the second puller wire 28B proximally. Each puller wire has a lubricious coating, e.g. of TEFLON®. The puller wires can be made of any suitable metal, such as stainless steel or Nitinol and the TEFLON coating imparts lubricity to the puller wire. Each puller wire may also extend through a respective protective sheath to prevent the puller wire from cutting into the fins 24A and 24B during deflection.

As shown in FIG. 5, space regions or quadrants span underneath the outer tubing 13 defined between adjacent struts 19 and fins 24. Longitudinally-aligned quadrants define or trace longitudinal "lumen-like" paths 30A, 30B, 30C and 30D that extend the length of the deflectable body 12 for receiving components, including lead wires, cables, and/or other tensile members. In the illustrated embodiment, lead wires 32T and 32R for the tip and ring electrodes 17 and 21 pass through quadrant path 30A. Thermocouple wires 44 and 45 pass through the quadrant path 30B. A cable 40 (including, e.g., wires connected to orthogonal sensing coils Cx, Cy and Cz of an electromagnetic (EM) position sensor housed in the distal section 15) pass through path 30C. The cable 40 may also include wires connected to coils of a force sensor (not shown) and/or position sensor (not shown) housed in the distal section 15. A suitable force sensor is described in U.S. Pat. No. 8,357,152, issued on Jan. 22, 2013 to Govari et al., entitled CATHETER WITH PRESSURE SENSING, and in U.S. Patent Publication No. 2011/0130648, to Beeckler et al., filed Nov. 30, 2009, entitled CATHETER WITH PRESSURE MEASURING TIP, both disclosures of which are incorporated herein by reference.

In some embodiments, the core 14 includes a longitudinal "lumen-like" path 50 formed in the core 14, which may be on-axis longitudinally relative to the spine 18. In the illustrated embodiment, the path 50 receives an irrigation tubing 46 for passing fluid to the tip electrode 17 of the distal section 15.

As shown in FIG. 3A and FIG. 3B, a distal end portion 19D of each of the struts 19A and 19B may be trimmed in some embodiments of the invention with an instep to provide a lesser circumference for insertion into a proximal end of a cylindrical housing of the force sensor. In this manner, the spine 18 and the force sensor are readily attached to each other and they remain on-axis with each other. Centering fins 47 may also be provided around the core 14 for insertion in a proximal end of a cylindrical housing of the force sensor.

Catheter Assembly

In assembling the catheter 10, any and all inserts 26 are placed in the notches 49 of the fins 24A, 24B, as needed for achieving the desired deflection curvature(s). Moreover, the irrigating tubing 46 is inserted through the path 50 in the core 14, and the puller wires 28A, 28B are inserted through the through-holes 22A, 22B, respectively. The electrode lead wires 32T, 32R and the thermocouple wires 44, 45 are positioned in the pathway 30A defined by the quadrants, and the cable 40 is positioned in the pathway 30B defined by quadrants. So assembled, a spine assembly comprising the spine 18 and one or more of the foregoing tensile components is then inserted into and through the outer tubing 13. In this manner, the tensile components including, e.g., the lead wires, cables and thermocouple wires, are supported by the spine 18 and thus less prone to breakage and damage when advanced through the lumen of the outer tubing 13.

Distal and proximal ends of the spine are trimmed or otherwise shaped for coupling with other components, including e.g., the tubing of the catheter body at the proximal end and the cylindrical member of the force sensor at the distal end. In the latter regard, the outer tubing may also cover the force sensor, or a distal end of the outer tubing is connected to another, shorter tubing cover for the force sensor.

Micro Injection Molding of the Spine

In some embodiments, with reference to and incorporation of the description above, the spine 18 is manufactured by processes that include providing a micro-mold assembly that forms a spine with one or more of the following:
(a) a core
(b) one or more struts
(b) one or more fins
(c) one or more quadrants The process may also include one or more of the following:
(a) providing the core with a passage therethrough
(b) providing each fin with a through-hole
(c) providing each fin with a notch configured to receive an insert
(d) providing a first set of fins and a second set of fins
1. wherein the first and second sets of fins are generally diametrically opposed to each other, and/or
2 wherein the first and second sets of fins are at generally the same longitudinal distances along the length of the spine or at different (offset) longitudinal distances along the length of the spine.
(e) providing at least a first strut and a second strut diametrically opposed to each other.
(f) configuring a strut with an enlarged free end.

The spine may be formed from any plastic or polymer suitable for formation by injection molding.

It is understood that the terms "injection-molding," "insert-molding," and "over-molding," (and variations thereof) are used interchangeably herein, as appropriate, to include any process wherein a material is injected into a mold cavity, where it cools and hardens to the configuration of the cavity in forming a molded component. In some applications, the mold cavity is configured to partially or fully cover a first material or substrate in forming the molded component. In some applications, the mold cavity is configured in or through a first material or substrate in forming the molded component. Combinations of these applications may be employed as appropriate or desired.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Notably, the drawings are not necessarily to scale, and any one or more features of any one or more embodiments may be included in any other one or more embodiments in addition to or in lieu of any feature, as desired or appropriate. Accordingly, the foregoing description should not be read as pertaining only to the precise structures described and illustrated in the accompanying drawings, but rather should be read consistent with and as support to the following claims which are to have their fullest and fair scope.

What is claimed is:

1. A deflectable catheter having:
an elongated catheter body having a spine constructed of a flexible material, and an outer cover circumferentially surrounding the spine along the length of the catheter body, the spine extending within the outer cover in a longitudinal direction and having:
a center core radially spaced from an inner wall of the outer cover, two opposing struts extending the length of the spine and extending outwardly from the core between the core and the outer cover in defining a plane P(a) generally bisecting the spine and the catheter body along the longitudinal direction into a portion N(a) and a portion N(b), the struts configured to resist deflection of the spine and the catheter body within the plane P(a) and bias deflection within a plane P(b) generally perpendicular to the plane P(a), and a first set of longitudinally-aligned fins along a first section of the spine, the first set of fins extending outwardly from the core between the core and the outer cover in the portion N(a) of the spine and coextensive with the plane P(b), each of the fins of the first set has a first predetermined length in the longitudinal direction and is separated from an adjacent fin of the first set by a first predetermined gap space to provide the spine with a first predetermined deflection curvature within the plane P(b) in the direction of the first set of fins in the first section of the spine, one of the two opposing struts and the first set of fins defining a longitudinal space therebetween and between the center core and the outer cover through which one or more components can longitudinally extend; and a control handle proximal of the catheter body, the control handle configured to deflect the catheter body.

2. The deflectable catheter of claim 1, further comprising a second set of longitudinally-aligned fins along the first section of the spine in the portion N(b), the second set of fins generally opposite of the first set of fins in the portion N(a) of the spine and generally coextensive with the second plane P(b).

3. The deflectable catheter of claim 2, wherein each of the fins of the second set has a second predetermined length in the longitudinal direction and is separated from an adjacent fin of the second set by a second predetermined gap space to provide the spine with a second predetermined deflection curvature within the plane P(b) in the direction of the second set of fins in the first section of the spine, wherein the second predetermined length is generally equal to the first predetermined length and the second predetermined gap space is generally equal to the first predetermined gap space.

4. The deflectable catheter of claim 2, wherein the spine is provided with a second predetermined deflection curvature within the plane P(b) in the direction of the second set of fins, wherein the second predetermined deflection curvature is generally equal to the first predetermined deflection curvature within the plane P(b) in the direction of the first set of fins.

5. The deflectable catheter of claim 2, wherein each of the fins of the second set has a second predetermined length in the longitudinal direction, wherein the second predetermined length is different from the first predetermined length of the first set of fins.

6. The deflectable catheter of claim 2, wherein each of the fins of the second set is separated from an adjacent fin of the second set by a second predetermined gap space, wherein the second predetermined gap space is different from the first predetermined gap space of the first set of fins.

7. The deflectable catheter of claim 2, wherein the spine is provided with a second predetermined deflection curvature within the plane P(b) in the direction of the second set of fins, wherein the second predetermined deflection curvature is different from the first predetermined deflection curvature within the plane P(b) in the direction of the first set of fins.

8. The deflectable catheter of claim 1, wherein one of the struts and the set of longitudinally-aligned fins define a quadrant space therebetween that is covered by a portion of the outer covering.

9. The deflectable catheter of claim 8, further comprising a tensile member passing through the quadrant space.

10. The deflectable catheter of claim 8, further comprising a tubing passing through the quadrant space.

11. The deflectable catheter of claim 1, further comprising an insert connecting at least two fins of the first set.

12. The deflectable catheter of claim 11, wherein the insert is received in a notch formed in each of the fins.

13. The deflectable catheter of claim 1, wherein the core has a through-hole in the longitudinal direction.

14. The deflectable catheter of claim 1, wherein the spine has another set of fins extending outwardly from the core in a second section of the spine and coextensive with the plane P(b), and each of the fins of the another set has another predetermined length in the longitudinal direction different from the first predetermined length of the fins of the first set.

15. The deflectable catheter of claim 1, wherein the spine has another set of fins extending outwardly from the core in a second section of the spine and coextensive with the plane P(b), and each of the fins of the another set is separated from an adjacent fin of the another set by another predetermined gap space that is different from the first predetermined gap space of the fins of the first set.

* * * * *